United States Patent
Cho

(10) Patent No.: US 10,528,810 B2
(45) Date of Patent: Jan. 7, 2020

(54) DETECTING USER VIEWING DIFFICULTY FROM FACIAL PARAMETERS

(71) Applicant: Samsung Electronics Co., Ltd., Suwon-si, Gyeonggi-do (KR)

(72) Inventor: Young Eun Cho, Middlesex (GB)

(73) Assignee: Samsung Electronics Co., Ltd., Suwon-si (KR)

( * ) Notice: Subject to any disclaimer, the term of this patent is extended or adjusted under 35 U.S.C. 154(b) by 8 days.

(21) Appl. No.: 15/880,383

(22) Filed: Jan. 25, 2018

(65) Prior Publication Data

US 2018/0150692 A1  May 31, 2018

Related U.S. Application Data

(63) Continuation of application No. 14/626,685, filed on Feb. 19, 2015, now Pat. No. 9,916,503.

(30) Foreign Application Priority Data

Feb. 20, 2014 (GB) .................................. 1403031.6

(51) Int. Cl.
| | |
|---|---|
| *G06K 9/00* | (2006.01) |
| *G09G 5/30* | (2006.01) |
| *A61B 3/11* | (2006.01) |
| *A61B 3/14* | (2006.01) |
| *A61B 3/113* | (2006.01) |

(52) U.S. Cl.
CPC .......... *G06K 9/00617* (2013.01); *A61B 3/113* (2013.01); *A61B 3/145* (2013.01); *G06K 9/00302* (2013.01); *G06K 9/00604* (2013.01); *G09G 5/30* (2013.01); *G06K 2009/00322* (2013.01); *G09G 2320/08* (2013.01); *G09G 2354/00* (2013.01); *G09G 2370/022* (2013.01)

(58) Field of Classification Search
USPC ......................................................... 345/581
See application file for complete search history.

(56) References Cited

U.S. PATENT DOCUMENTS

| | | | |
|---|---|---|---|
| 2011/0131041 A1* | 6/2011 | Cortez .................. | G06T 13/205 704/235 |
| 2012/0321759 A1* | 12/2012 | Marinkovich ....... | A61B 5/0531 426/231 |
| 2013/0250086 A1* | 9/2013 | Mar .................... | G02B 27/0093 348/78 |
| 2015/0334292 A1* | 11/2015 | Tartz ........................ | G08B 6/00 348/222.1 |
| 2016/0162728 A1* | 6/2016 | Arai ........................ | A61B 5/743 382/118 |

* cited by examiner

*Primary Examiner* — Wesner Sajous

(57) ABSTRACT

A method to determine whether a user is experiencing difficulty visually resolving content is disclosed. The method includes capturing one or more images of the user while the user is viewing the content. The method also includes obtaining facial parameters related to a visual acuity of the user from the captured one or more images. The method further includes determining whether the user is experiencing difficulty visually resolving the content based on the obtained one or more facial parameters. The method is implemented in a device such as a smartphone, tablet computer, or television. The facial parameters include information about the extent to which the user has their eyes open or closed, whether the user is wearing glasses, and the distance at which the user is viewing the content.

18 Claims, 5 Drawing Sheets

DETECTING USER VIEWING DIFFICULTY FROM FACIAL PARAMETERS

PRIORITY

This application is a continuation of U.S. application Ser. No. 14/626,685, filed Feb. 19, 2015, which claims foreign priority under 35 U.S.C. § 119(a) to a GB patent application filed in the United Kingdom Intellectual Property Office on Feb. 20, 2014 and assigned Serial No. GB 1403031.6, the entire disclosures of which are hereby incorporated by reference.

TECHNICAL FIELD

The present disclosure relates to a method and apparatus for determining whether a user is experiencing difficulty visually resolving content displayed on a display.

BACKGROUND

Many modern devices include some form of display, such as a flatscreen or projector, for displaying content. To ensure that displayed content can be clearly seen by a user in varying lighting conditions, many devices include an ambient light sensor to detect the ambient brightness and adapt the display brightness accordingly. In bright conditions, the display brightness is increased to ensure that high contrast is maintained, whereas in dim conditions the display brightness is decreased to conserve power. However, even in similar viewing conditions, the user experience can vary from one person to the next. For example, one person may be able to easily read displayed text under certain conditions, whereas a user with poor eyesight may struggle to read the same displayed text under the same conditions. Such individual factors are not taken into account by conventional systems.

SUMMARY

To address the above-discussed deficiencies, it is a primary object to provide a method to determine whether a user is experiencing difficulty in visually resolving content displayed on a display is provided. The method includes capturing an image of the user viewing the content displayed on the display. The method also includes obtaining, from the captured image, one or more facial parameters related to a visual acuity of the user. The method further includes determining whether the user is experiencing difficulty visually resolving the content based on the obtained one or more facial parameters.

Determining whether the user is experiencing difficulty visually resolving the content can includes obtaining a visual acuity score based on the obtained one or more facial parameters. Determining whether the user is experiencing difficulty visually resolving the content also includes in response to the visual acuity score exceeding a threshold value, determining that the user is experiencing difficulty visually resolving the content. The threshold value is determined based on historical visual acuity data for the user. The method further includes tracking the visual acuity score of the user over time. The method also includes in response to the visual acuity score continuously exceeding the threshold value for a predetermined length of time, determining that the user is experiencing difficulty visually resolving the content.

The method further includes obtaining sensor data from one or more sensors. The visual acuity score is obtained based on the sensor data and the one or more facial parameters. Obtaining the sensor data from one or more sensors includes obtaining acceleration data from an accelerometer, or obtaining orientation data from a gyroscope, or obtaining heart rate data from a heart rate sensor. Determining whether the user is experiencing difficulty visually resolving the content includes comparing one of the obtained one or more facial parameters to a corresponding threshold value for the one of the one or more facial parameters and in response to said one of the one or more facial parameters exceeding the threshold value, determining that the user is experiencing difficulty visually resolving the content.

The one or more facial parameters include a change in the visible area of one or both of the user's eyes in a plurality of images captured over time. The one or more facial parameters include a distance parameter relating to a distance between the user and the display. The distance parameter is obtained based on the apparent size of the user's face in the captured image. The one or more facial parameters include one or more demographic parameters relating to the user. Obtaining the one or more demographic parameters from the captured image include analyzing the captured image using a face detection algorithm. The one or more facial parameters include a glasses parameter indicating whether the user is wearing glasses.

Prior to determining whether the user is experiencing difficulty visually resolving the content, the method further includes determining whether the user is currently viewing the content on the display. The determination whether the user is experiencing difficulty visually resolving the content may only be performed in response to a determination that the user is viewing the content on the display. The displayed content includes text. Determining whether the user is currently viewing the content includes detecting an eye scroll pattern by performing eye tracking using a plurality of images of the user captured while the text is displayed and comparing the detected eye scroll pattern to an expected eye scroll pattern for the displayed text. In response to a determination that the user is currently experiencing difficulty visually resolving the content, the method further includes controlling the display to change the size of text or images shown on the display, or to change the brightness or contrast of the display.

The method further includes determining a type of viewing difficulty being experienced by the user. The method includes selecting display settings according to the type of viewing difficulty determined. The method also includes controlling the display according to the selected display settings. The image of the user includes a video of the user. The one or more facial parameters are obtained from the captured video. The image of the user viewing the content is obtained by capturing the image at a client device. Determining whether the user is experiencing difficulty visually resolving the content includes transmitting the obtained one or more facial parameters from the client device to a server and receiving a response at the client device from the server. The response indicates whether the user is experiencing difficulty visually resolving the content. Obtaining the image of the user viewing the content includes receiving the image at a server, from a client device. The method further includes transmitting a message from the server to the client device indicating that the user is experiencing difficulty visually resolving the content, in response to a determination that the user is experiencing difficulty visually resolving the content.

A computer-readable storage medium is arranged to store a computer program which, when executed, performs the method. According to the present disclosure an apparatus is provided. The apparatus includes a display. The apparatus also includes a camera configured to capture an image of a user while the user is viewing content displayed on the display. The apparatus further includes an image processor configured to obtain, from the captured image, one or more facial parameters related to a visual acuity of the user. The apparatus includes a controller configured to determine whether the user is experiencing difficulty visually resolving the content based on the obtained one or more facial parameters.

The controller is configured to obtain a visual acuity score based on the obtained one or more facial parameters and to determine that the user is experiencing difficulty visually resolving the content in response to the visual acuity score exceeding a threshold value. The controller is configured to determine the threshold value based on historical visual acuity data for the user.

The controller is configured to track the visual acuity score of the user over time and to determine that the user is experiencing difficult visually resolving the content in response to the visual acuity score continuously exceeding the threshold value for a predetermined length of time. The controller is configured to obtain sensor data from one or more sensors and to obtain the visual acuity score based on the sensor data and the one or more facial parameters. The controller is configured to obtain the sensor data by obtaining acceleration data from an accelerometer, or obtaining orientation data from a gyroscope, or obtaining heart rate data from a heart rate sensor.

The controller is configured to compare one of the obtained one or more facial parameters to a corresponding threshold value for said one of the one or more facial parameters and to determine that the user is experiencing difficulty visually resolving the content in response to said one of the one or more facial parameters exceeding the threshold value. The image processor is arranged to obtain a distance parameter based on the apparent size of the user's face in the captured image, or to obtain one or more demographic parameters by analyzing the captured image using a face detection algorithm, or to obtain a glasses parameter indicating whether the user is wearing glasses. The controller is further configured to determine whether the user is currently viewing the content on the display and to only determine whether the user is experiencing difficulty visually resolving the content in response to a determination that the user is viewing the content on the display.

The displayed content includes text, and the apparatus further includes an eye tracking unit configured to detect an eye scroll pattern from a plurality of images of the user captured while the text is displayed. The controller is configured to determine whether the user is currently viewing the content by comparing the detected eye scroll pattern to an expected eye scroll pattern for the displayed text. In response to a determination that the user is currently experiencing difficulty visually resolving the content, the controller is further configured to control the display to change the size of text or images shown on the display, or to change the brightness or contrast of the display.

The apparatus is further configured to determine a type of viewing difficulty being experienced by the user. The apparatus is configured to select display settings according to the type of viewing difficulty determined. The apparatus is also configured to control the display according to the selected display settings. The captured image includes video of the user. The image processor is configured to obtain the one or more facial parameters from the captured video. The apparatus further includes a network interface for communicating with a server. The controller is configured to determine whether the user is experiencing difficulty visually resolving the content by transmitting the obtained one or more facial parameters to the server and receiving a response from the server. The response indicating whether the user is experiencing difficulty visually resolving the content. The apparatus is included in user equipment configured for use in a mobile communications system, such as a smartphone or tablet computer.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION

FIGS. 1 through 7, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged electronic device.

Figure 1:
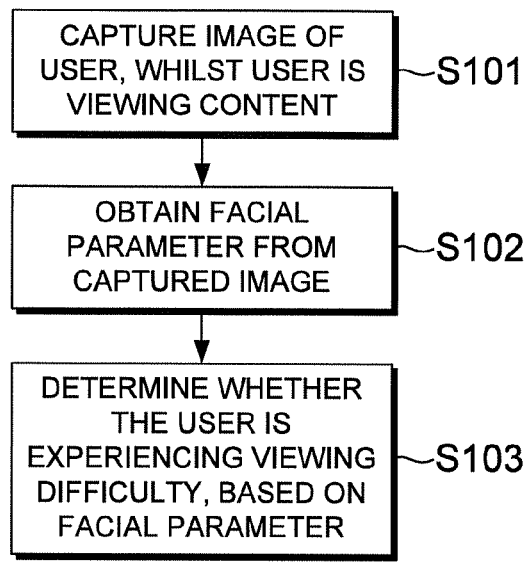
FIG. 1 is a flowchart illustrating an example method of determining whether a user is experiencing difficulty visually resolving content displayed on a display according to this disclosure.

FIG. 1 is a flowchart illustrating an example method of determining whether a user is experiencing difficulty visually resolving content displayed on a display according to this disclosure. The method is implemented by any system which includes a display for displaying content, and a camera arranged to capture an image of the user whilst the user is viewing content on the display. In the present embodiment the method of FIG. 1 is implemented in a smartphone 200, illustrated in FIG. 2, including a display 201 and a forward-facing camera 202.

First, in step S101 the camera 202 is used to capture an image of the user, whilst the user is viewing content displayed on the display 201. Depending on the embodiment, the image is captured while any content is being displayed, or when specific content is being displayed. An example of specific content is pre-programmed text or images to be used for diagnostic purposes.

Next, in step S102 a facial parameter related to a visual acuity of the user is obtained from the captured image. Here, by 'visual acuity' it is meant the visual acuity of the user under current viewing conditions. Therefore the visual acuity is determined not only by the user's physiology, but also by external factors such as ambient light levels. Although a single facial parameter is obtained in the present embodiment, in other embodiments a plurality of different facial parameters could be obtained.

In an embodiment the facial parameter relates to the user eye area in the captured image, that is, the visible area of one or both of the user's eyes. This is only one example of a type of facial parameter that is used, and in other embodiments, different facial parameters can be used. The facial parameter is obtained by using a face detection algorithm to detect the user's face in the captured image, and to determine where the user's eyes are located in the captured image. The facial parameter relating to the user eye area takes various forms, including a ratio between the width and height of each eye in the image (an aspect ratio), an absolute area (such as in pixels) of each eye, or a relative area of each eye relative to the total area of the user's face in the captured image. Examples of different facial parameters will be described in more detail later.

Then, in step S103 it is determined whether the user is experiencing difficulty visually resolving the content, based on the obtained facial parameter. In an embodiment, the facial parameter relating to the user eye area indicates the extent to which the user's eyes are open or closed. A normal range of values are defined, which is pre-programmed or is learned over time by monitoring the user's normal appearance when viewing the display. When a value is detected that falls outside this range, it is taken as an indicator that the user is having difficulty viewing the display. For example, a value indicating that the user's eyes are closed further than would normally be expected indicates that the user is squinting to read text on the display. Also, a value indicating that the user's eyes are open further than would normally be expected indicates that the user is struggling to see the display clearly, for example if the display brightness is too low.

Various further actions can be taken in response to a determination that the user is experiencing difficulty visually resolving the content. For example, the value of the facial parameter is logged and uploaded to a healthcare server to be monitored by a physician. As another example, a message is displayed to the user to recommend that they arrange to have their eyesight checked by a physician.

The display is reconfigured to improve viewing conditions, by using new display settings to change the way in which content is displayed. The display is reconfigured automatically, or the device requests the user to confirm whether or not the display should be reconfigured. In some embodiments, an accessibility menu screen in the device's user interface is shown to allow the user to manually select new display settings. Examples of ways in which the display is reconfigured include enlarging the size of images on the display, increasing the display brightness, and changing the font type, size, color, or weight. Any of these exemplary actions can be performed, alone or in combination, in any embodiment.

In some embodiments, the method further includes steps of determining a type of viewing difficulty being experienced by the user, based on the facial parameters, and selecting display settings according to the determined type of viewing difficulty. The display settings are used when reconfiguring the display, and are, for example, stored locally or retrieved from a server. For example, the server stores the display settings most commonly selected by different users for the different types of viewing difficulty. Whenever a type of viewing difficulty is detected and the user manually selects new display settings, information about the selected display settings is uploaded to the server and stored. Examples of types of viewing difficulty that is detected in embodiments of the disclosure include long-sightedness or short-sightedness, which is determined according to the distance at which the user is holding the screen from their face. As another example, if the user is squinting it is determined that the user is struggling to see the display against very bright background light, and the display brightness is increased accordingly.

In some embodiments, after reconfiguring the display, the method of FIG. 1 is repeated to determine whether the user is still experiencing viewing difficulty with the new display settings. In some embodiments, the value of an obtained facial parameter is tracked over time by capturing a plurality of images, and the determination in step S103 is based on changes in the facial parameter over a time period. A sharp increase or decrease in the value of the facial parameter indicates deterioration in the user's visual acuity, which can be health-related. In such cases, a warning message could be presented to the user, via the display or otherwise, or a notification could be uploaded to the user's account on a healthcare server.

In embodiments in which the orientation of the camera and the display are fixed with respect to one another, the camera should be orientated so as to face the user when the user is in the intended viewing position for the display. In many embodiments this will mean that the camera and the display face in the same direction, for example in a smartphone or tablet computer embodiment, but this is not essential. An example of an embodiment in which the display and camera face in different directions is a heads-up-display (HUD) based system integrated in an automobile dashboard, in which the display arranged to face vertically upwards towards the windscreen, and the camera is arranged to face horizontally towards the driver's seating position. Furthermore, in some embodiments the orientation between the camera and the display is not fixed, for example in a video-conferencing system including a moveable video camera and a physically separate display.

By 'camera', it is meant any image capture device which is capable of capturing an image of a user. For example, suitable image capture devices include a charge-coupled device (CCD) sensor, a complementary metal oxide semiconductor (CMOS) sensor, or an N-type metal oxide semiconductor (NMOS) sensor. Depending on the embodiment, the camera capture one or more still images of the user, or capture continuous video of the user. Hereinafter, references to 'an image' of the user should be understood as encompassing both still and moving images.

Embodiments of the disclosure are implemented in any device which includes an image capture device capable of capturing an image of the user whilst the user is viewing content on a display. For example, in an embodiment of the disclosure the method of FIG. 1 is implemented in a smartphone device including a forward-facing camera for video calling. In another embodiment, the method is implemented in a laptop or tablet computer which includes a webcam. Also, many televisions now include forward-facing video cameras for use in Internet-based video calling, or for use in gesture-recognition based control systems, and so in some embodiments of the present disclosure the method of FIG. 1 is implemented in a television. In yet another embodiment, the method is implemented in a video-conferencing system including a display and a moveable video camera that is controlled to face a user participating in a video conference. It will be appreciated that the aforementioned devices are provided as illustrative examples only, and the disclosure is not restricted to these particular types of device.

Figure 2:
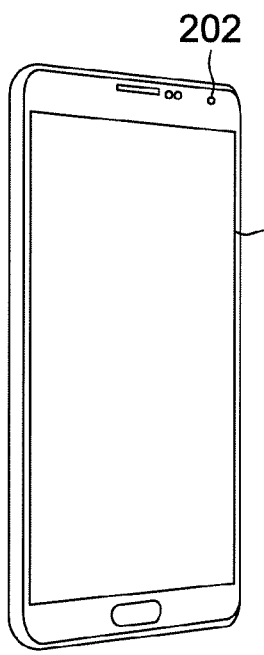
FIG. 2 illustrates an example apparatus according to this disclosure.

FIG. 2 illustrates an example apparatus according to this disclosure. For example, FIG. 2 illustrates apparatus configured to implement the method of FIG. 1. In an embodiment, the apparatus is a smartphone 200 including a flat-panel display 201, such as a touchscreen, and a forward-facing camera 202 arranged to capture an image of the user while the user is viewing content on the display 201. It will be understood from the foregoing description that the disclosure is not limited to smartphone embodiments, and in other embodiments the method is implemented in other types of device.

Figure 3:
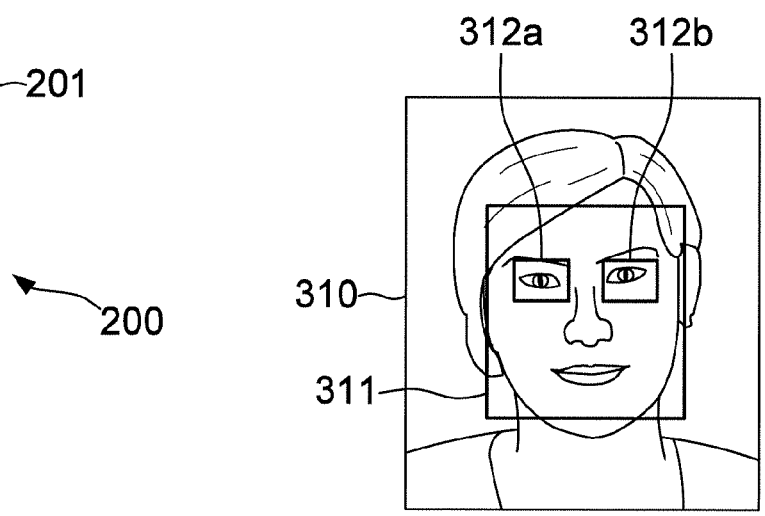
FIG. 3 illustrates an example image processing method for obtaining facial parameters from an image of a user according to this disclosure.

FIG. 3 illustrates an example image processing method for obtaining facial parameters from an image of a user according to this disclosure. The image processing method is used to obtain a facial parameter relate to the user eye area, as described above with reference to FIG. 1, or is used to obtain other types of facial parameter.

As shown in FIG. 3, the image 310 is processed using a face detection algorithm to detect a face area 311 within the image, and to detect eye areas 312a, 312b within the face area 311. The pixels within the eye areas 312a, 312b then are analyzed to obtain a value of the facial parameter, as described herein.

Other examples of facial parameters that are detected from the captured image 310 include, but are not limited to, a distance parameter relating to a distance between the user and the display, one or more demographic parameters relating to the user, and a glasses parameter indicating whether the user is wearing glasses. The distance parameter is used to determine whether the user is too close or too far from the display, either of which indicate that the user is experiencing viewing difficulty.

In some embodiments, a face recognition algorithm is used to detect certain types of expression or facial movements that indicate viewing difficulty. For example, frowning, or wrinkling of the skin near the eyes indicating squinting, is a sign that the user is experiencing viewing difficulty. In such embodiments, the facial parameter includes one or more flags for different predefined facial characteristics that are indicative of a user experiencing viewing difficulty. The value of a flag is set to 'TRUE' if that facial characteristic has been detected, and it is determined that the user is experiencing viewing difficulty if a threshold number (such as one or more) of the flags in the facial parameter are set to 'TRUE'. For example, the facial parameter includes two flags relating to frowning and wrinkling near the eyes, and if both flags are 'TRUE' it is determined that the user is experiencing viewing difficulty.

For example, the distance parameter is obtained based on the apparent size of the user's face in the captured image. If the apparent size of the face, which can be measured in terms of linear dimensions or an area, is greater than a maximum threshold value as a fraction of the total image size, it is determined that the user is too close to the display. Similarly, if the apparent size of the face is lower than a minimum threshold value as a fraction of the total image size, it is determined that the user is too far from the display. In either of these outcomes, it is assumed that the user is experiencing difficulty visually resolving the displayed content. On the other hand, if the apparent size of the face is between the minimum and maximum thresholds, it is assumed that the user is not experiencing viewing difficulty.

The demographic parameters include, for example, estimates of the user's age, gender or race. These are used to determine whether the user falls into any demographic categories associated with a high risk of eyesight problems. For example, in some embodiments it is assumed that the user is experiencing viewing difficulty, in response to a determination that the user is in a high risk demographic category. In such embodiments, corrective action, such as increasing the display brightness, or font and image sizes, is taken automatically without checking other facial parameters.

Figure 4:
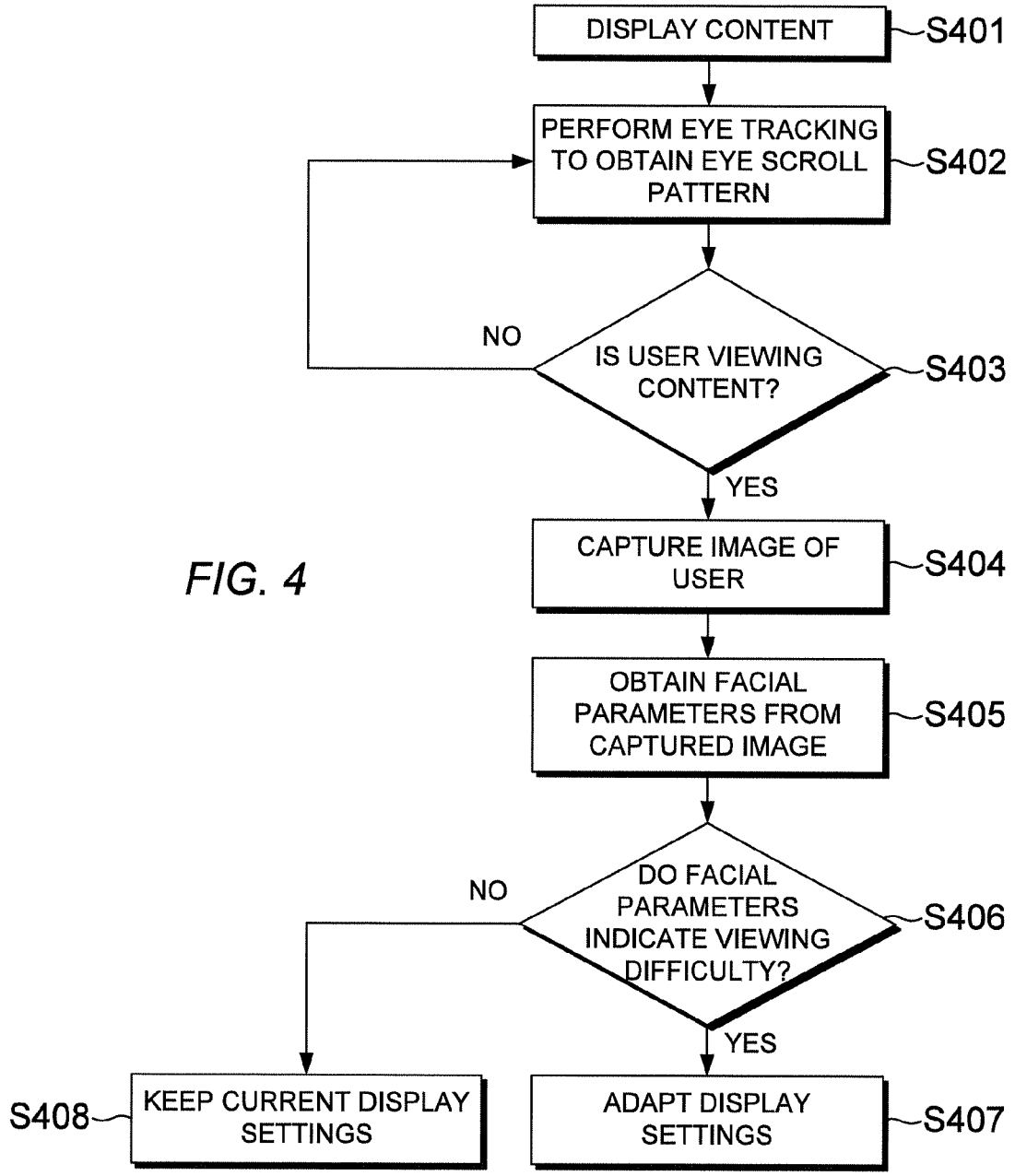
FIG. 4 is a flowchart illustrating an example method of automatically detecting user viewing difficulty and adapting display settings according to this disclosure.

FIG. 4 is a flowchart illustrating an example method of automatically detecting user viewing difficulty and adapting display settings according to this disclosure. In the method shown in FIG. 4, steps S404, S405 and S406 are similar to steps S101, S102 and S103. However, prior to determining whether the user is experiencing difficulty visually resolving the content, it is first checked whether the user is viewing the displayed content. This avoids processing time and power being wasted unnecessarily by attempting to detect viewing difficulty when the user is not currently viewing the displayed content.

First, in step S401 the content is displayed. In an embodiment, the displayed content includes text. For example, the displayed content is a webpage or a text message. Then, while the content is being displayed, in step S402 eye tracking is used to detect an eye scroll pattern of the user. Next, in step S403 it is checked whether the user is currently viewing the displayed content. In an embodiment, step S403 is performed by comparing the detected eye scroll pattern to an expected eye scroll pattern for the displayed text. In response to the detected eye scroll pattern matching the expected eye scroll pattern, within a certain margin of error, it is determined in step S403 that the user is currently viewing the content, and the method proceeds to obtain and process the facial parameters in steps S404, S405 and S406. On the other hand, if the user is not viewing the content, then the method returns to step S402 and waits for a determination that the user is viewing the content, before proceeding further.

The expected eye scroll pattern is a general pattern applicable to any displayed text, or is specific to the content of the text being displayed. For example, a general eye scroll pattern for English text would be a pattern of scanning lines from left to right, and top to bottom. A more specific eye scroll pattern can take into account the distribution of text on the screen, for example the spacing between paragraphs of text.

Although eye tracking is used in the present embodiment, in other embodiments a different technique is used in steps S402 and S403 to determine whether the user is currently viewing the content. As an example, in an alternative embodiment an image of the user is captured and processed using a face detection algorithm to determine a direction in which the user is facing, relative to the display. In response to a determination that the user is not currently facing directly at the display, it is assumed that the user is not currently viewing the displayed content.

In some embodiments, eye tracking in step S402 is performed by capturing and analyzing a sequence of images of the user. In such embodiments, the separate step of capturing an image (S404) is omitted, and in step S405 the facial parameters is obtained using one or more images captured during the eye tracking process in step S402.

In addition, in the present embodiment the display settings are automatically adapted in step S407, in response to a determination in step S406 that the user is experiencing viewing difficulty. Automatically reconfiguring the display in this way improves the user viewing experience, without requiring user intervention. If, on the other hand, it is determined that the user is not experiencing viewing difficulty, then in step S408 the current display settings are retained. As described above, in some embodiments different actions are taken after step S406, and accordingly steps S407 and S408 can be omitted.

Figure 5:
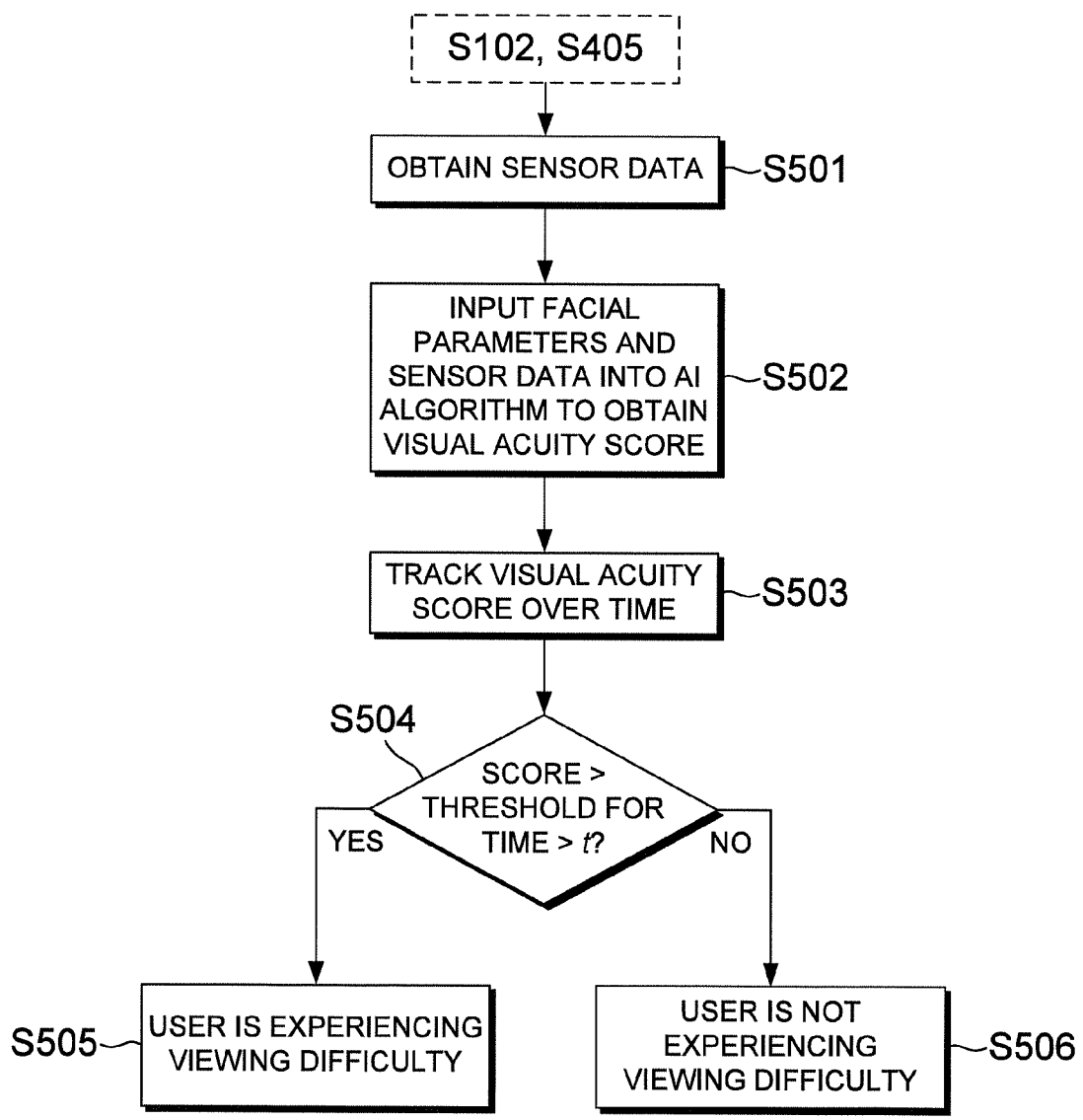
FIG. 5 is a flowchart illustrating an example artificial-intelligence-based method of determining whether a user is experiencing difficulty visually resolving displayed content according to this disclosure.

FIG. 5 is a flowchart illustrating an example artificial-intelligence-based method of determining whether a user is experiencing difficulty visually resolving displayed content according to this disclosure. The method steps illustrated in FIG. 5 can, for example, be used at step S103 of FIG. 1 or step S406 of FIG. 4 to determine whether the user is experiencing viewing difficulty.

In step S501, sensor data is obtained from one or more sensors. In step S502, the sensor data and one or more facial parameters are inputted into an AI algorithm configured to output a numerical value, which is referred to as a 'visual acuity score'.

Examples of types of sensor data that are obtained include acceleration data from an accelerometer, orientation data from a gyroscope, and heart rate data from a heart rate sensor. Such sensors are often integrated into many devices, including smartphones and tablet computers. Although in the present embodiment sensor data is incorporated into the visual acuity score in step S502, in other embodiments the sensor data is omitted, and the visual acuity score is obtained solely on the basis of one or more facial parameters.

In the present embodiment the decision process also takes into account sensor data obtained from one or more sensors included in the device, for example accelerometer data. However, in other embodiments the sensor data is omitted, and the visual acuity score is obtained solely on the basis of one or more facial parameters.

Next, in step S503 the visual acuity score is tracked over time. This step includes periodically obtaining an updated value of the visual acuity score and storing the individual historical values of the visual acuity score. For example, a predefined maximum number of values are stored, and once this limit is reached, the oldest value is deleted from memory each time a new value is calculated and stored. Alternatively, instead of storing individual values over time, an average value could be stored and updated periodically.

Then, in step S504 it is checked whether the visual acuity score has continuously exceeded a threshold value for a predetermined length of time (t). Here, depending on how the visual acuity score is calculated, the threshold is a minimum or a maximum. The threshold is a pre-programmed value, or is determined based on historical visual acuity data for the user. For example, the threshold value is set as a percentage of the user's mean visual acuity score over a certain time.

In response to the visual acuity score remaining above a maximum threshold value, or below a minimum threshold value, for at least the predetermined time period, then the method proceeds to steps S505 and determines that the user is experiencing difficulty visually resolving the content. On the other hand, if the visual acuity score is within the acceptable limits in step S504, then the method proceeds to step S506 and determines that the user is not experiencing viewing difficulty.

The use of the predetermined time period t in step S504 ensures that the system only responds to a sustained deterioration in the visual acuity score, and does not respond to transient changes which might occur briefly due to a temporary change in viewing conditions. For example, the predetermined time period t is one week. However, in some embodiments step S503 is omitted, and in step S504 it is determined that the user is experiencing viewing difficulty as soon as the current value of the visual acuity score exceeds the threshold limit.

Although an AI algorithm is used to convert the facial parameters and sensor data into a visual acuity score, embodiments of the present disclosure are not limited to this approach. For example, in other embodiments, a fuzzy logic algorithm, a simple binary decision logic algorithm, or a hybrid method incorporating a combination algorithm is used. An example of a decision-based method will now be described with reference to FIG. 6.

Figure 6:
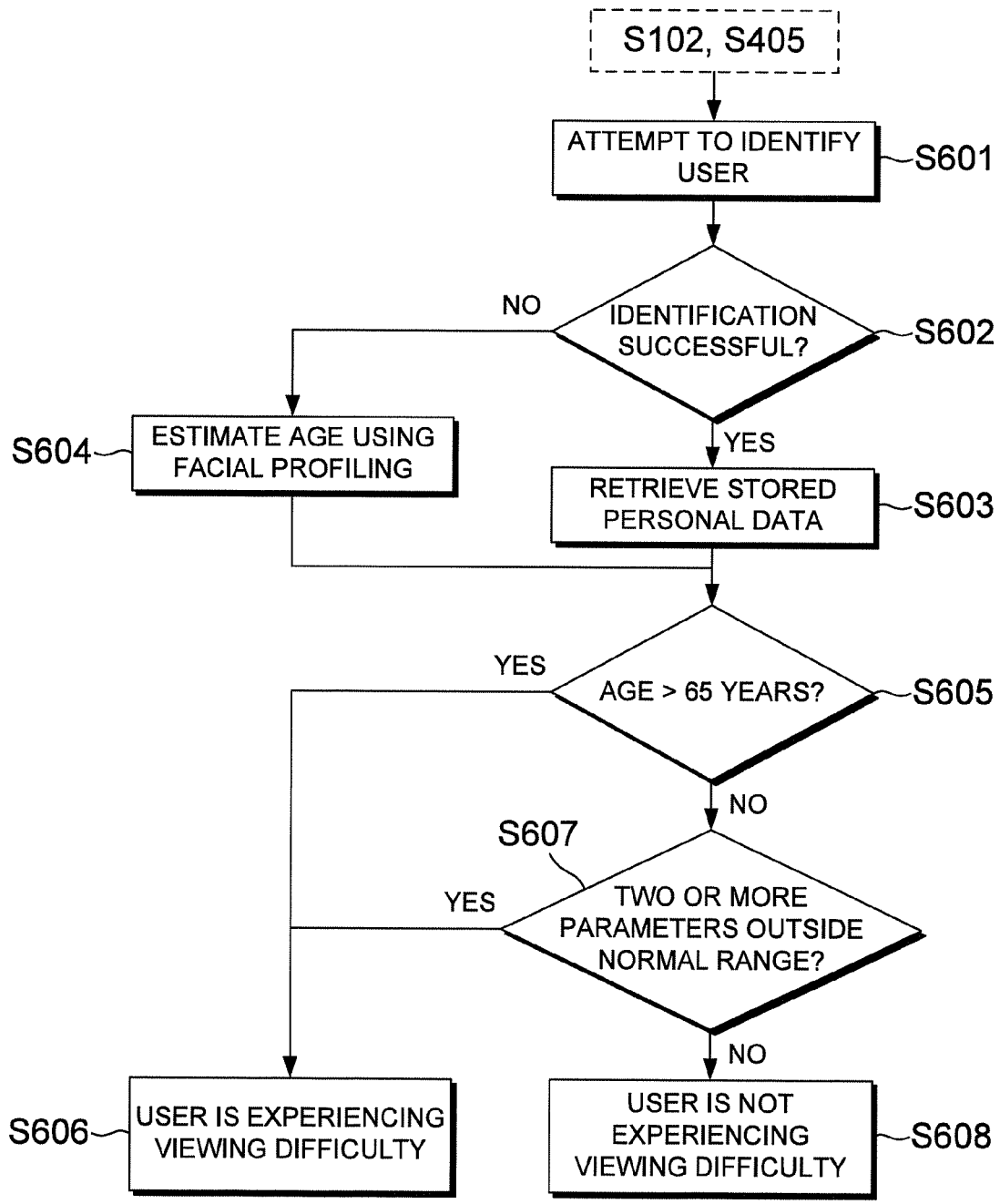
FIG. 6 is a flowchart illustrating an example decision-based method of determining whether a user is experiencing difficulty visually resolving displayed content according to this disclosure.

FIG. 6 is a flowchart illustrating an example decision-based method of determining whether a user is experiencing difficulty visually resolving displayed content according to this disclosure. Like the method of FIG. 5, the method steps illustrated in FIG. 6 is used at step S103 of FIG. 1 or step S406 of FIG. 4 to determine whether the user is experiencing viewing difficulty.

First, in step S601 an attempt is made to identify the current user. For example, user recognition is performed by face recognition, voice recognition, or by an input user ID such as an email login.

In step S602, it is checked whether the identification is successful. If the current user has been identified, then in step S603 personal data is retrieved for the user, including the user's age. On the other hand, if identification was not successful, then in step S604 an age is estimated for the user based on facial profiling.

Next, in step S605 the age obtained in step S603 or S604 is compared to a pre-programmed threshold, which in the present example is 65 years. In response to the age exceeding the threshold in step S605, then in step S606 it is assumed that the user is experiencing viewing difficulty, and appropriate action is taken. On the other hand, if the age is below the threshold in step S605, then the method proceeds to step S607 and considers other facial parameters.

In the present embodiment, the facial parameters analysed in step S607 include a distance parameter relating to a distance between the user and the display, an eye area parameter relating to the apparent size of the user's eyes relative to their face in the captured image, and a glasses parameter indicating whether the user is wearing glasses. For each parameter, a normal value or range of values is defined. For example, maximum and minimum thresholds are defined for the distance parameter based on the distance at which the current user normally holds the display, or based on typical viewing distances if the current user was not able to be identified in step S601. The normal value for the glasses parameter is a simple true or false Boolean value, indicating whether or not the user normally wears glasses. Also, a normal range of values is defined for the eye area parameter, which again is individual for the current user or is typical values if the user has not been identified.

In response to a predefined number of the parameters being outside their normal value or range of values in step S607, then the method proceeds to step S606 and concludes that the user is experiencing viewing difficulty. In response to a predefined number of the parameters being within their normal value or range of values in step S607, then the method proceeds to step S608 and concludes that the user is not experiencing viewing difficulty.

In the present embodiment, two or more parameters must be outside the normal value or range in order to trigger a determination that the user is experiencing viewing difficulty. In other embodiments, any number is set as the minimum number of facial parameters that must be out of range in order to trigger the determination. This approach takes into account the possibility that an unusual value for a single facial parameter not be the direct result of viewing difficulty. However, when several unusual values are detected at the same time, this is taken as strong circumstantial evidence that the user is experiencing viewing difficulty.

In the method of FIG. 6, a sequence of binary logic decision steps are illustrated for determining whether the user is experiencing difficulty visually resolving the displayed content. Although several parameters are considered in the present embodiment, a similar logic is applied to other embodiments with different numbers of parameters. In the simplest case, a single facial parameter is obtained and compared to a threshold value, and a determination made that the user is experiencing difficulty visually resolving the content in response to said facial parameter exceeding the threshold value.

Figure 7:
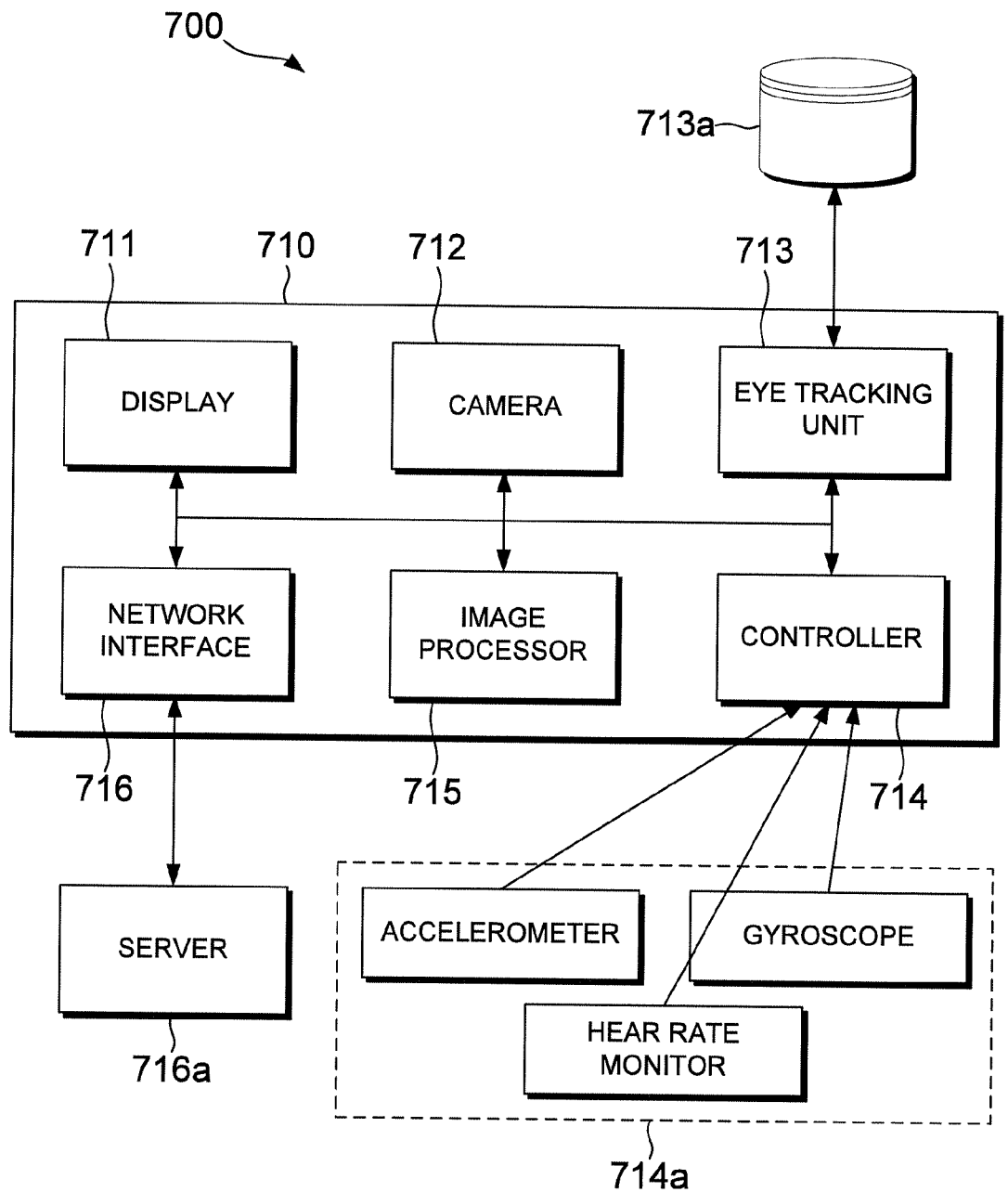
FIG. 7 illustrates an example apparatus according to this disclosure.

FIG. 7 illustrates an example apparatus according to this disclosure. The apparatus 700 can perform any of the above-described methods to determine whether a user is currently experiencing difficulty visually resolving displayed content.

As shown in FIG. 7, the apparatus 700 includes as a device 710 such as a smartphone, tablet computer, or television, and several remote elements 713a, 714a, 716a which communicate remotely with the device 710. In the present embodiment the device 710 is a smartphone such as the one illustrated in FIG. 2. However, in other embodiments some or all of the remote elements 713a, 714a, 716a are included within the device 710.

In the present embodiment, the device 710 comprises a display 711, a camera 712, an eye tracking unit 713, a controller 714, an image processor 715, and a network interface 716. In some embodiments, depending on the method implemented in the device 710, the eye tracking unit 713 and network interface 716 is omitted. In the present embodiment, the eye tracking unit 713, controller 714, and image processor 715 are embodied in the form of one or more software programs including software instructions which perform the appropriate functions, when executed on one or more processors. However, the disclosure is not limited to this arrangement, and various elements illustrated in FIG. 7 are embodied using hardware or software, or a combination of hardware and software. For example, although the eye tracking unit 713, controller 714, and image processor 715 are implemented in software in the present embodiment, in other embodiments one or more of these elements is embodied using dedicated hardware such as an application-specific integrated circuit (ASIC).

The camera is configured to capture an image of a user, whilst the user is viewing content displayed on the display 711. For example, as described above, the camera 712 is in a fixed position relative to the display 711, or is controllable to point towards the user whilst the used is viewing content on the display 711. In the present embodiment, the apparatus 710 is a smartphone, the display 711 is a touch screen display, and the camera 712 is a fixed forward-facing camera.

The image processor is configured to obtain, from the captured image, one or more facial parameters related to a visual acuity of the user. The image processor is used to perform step S101 of FIG. 1 and step S405 of FIG. 4. The controller 714 is configured to determine whether the user is experiencing difficulty visually resolving the content, based on the obtained one or more facial parameters. The controller 714 can, for example, be used to perform a method such as the one shown in FIG. 5 or FIG. 6.

In embodiments in which the controller 714 obtains a visual acuity score based on sensor data, in addition to the facial parameters, the controller 714 receives the sensor data from a plurality of sensors 714a. An accelerometer, gyroscope and heart rate monitor are shown in FIG. 7, but embodiments of the disclosure are not limited to these particular sensors. The controller 714 receives the sensor data over a wired connection or a wireless connection, and the sensors 714a is physically separate from the device 710 or is included in the device 710.

In the present embodiment, the controller 714 uses the eye tracking unit 713 to determine whether the user is currently viewing the content on the display 711, using a method such as the one described above with reference to FIG. 4. The eye tracking unit 713 optionally communicates with a remote database 713a to retrieve an expected eye scroll pattern for the content currently being displayed. In some embodiments, the eye tracking unit 713 is omitted, for example if the controller 714 uses a different method to determine whether the user is viewing the content, or does not perform the check at all.

The controller 714 uses the network interface 716 to communicate with a remote server 716a. This allows certain steps of the above-described method to be performed remotely, instead of being performed locally at the apparatus 710. For example, in some embodiments the controller 714 transmits the facial parameters obtained by the image processor 715 to the server 716a. The server 716a determines whether or not the user is experiencing viewing difficulty, and inform the controller 714 of the result by sending a response to the apparatus 710, indicating whether the user is experiencing difficulty visually resolving the content.

Furthermore, in some embodiments the image processor 715 is omitted from the device 710, and the controller 714 transmits the captured image or sequence of images to the remote server 716a for processing. The server 716a obtains the facial parameters from the received images, and either send the facial parameters back to the device 710 to be analysed by the controller 714, or determine whether the user is experiencing viewing difficulty and transmit a result of the determination to the device 710. In other embodiments, all steps of the method are performed locally, in which case the server 716*a* is not required.

Examples of various methods according to embodiments of the present disclosure have been described above. These methods are performed by dedicated hardware, for example an application specific integrated circuit (ASIC) configured to execute the method, by software instructions executed on a general-purpose processor, or by a combination of both software and hardware. The software instructions are in the form of one or more computer programs, stored in a computer-readable storage medium. In some embodiments, the software instructions are provided in the form of a downloadable application. The application could then be downloaded and installed on a conventional device such as a smartphone or tablet computer, to produce a modified device capable of implementing any of the above-described methods.

While certain embodiments of the disclosure have been described herein with reference to the drawings, it will be understood that many variations and modifications will be possible without departing from the scope of the disclosure as defined in the accompanying claims.

What is claimed is:

1. A method for operating an electronic device, the method comprising:
   obtaining, by at least one processor, an image of a face of a user viewing a first content;
   obtaining, by the at least one processor, information regarding a wrinkle on a skin of the user based on an analysis on the obtained image using an algorithm; and
   displaying, by the at least one processor, a second content on a display, wherein the second content is a content in which the first content is enlarged according to the information regarding the wrinkle,
   wherein the displaying the second content comprises:
      using an artificial intelligence (AI) algorithm based on the information regarding the wrinkle, and
      displaying the second content according to an output of the AI algorithm.

2. The method of claim 1, further comprising:
   determining that the user views the first content displayed on the electronic device by an eye tracking;
   detecting an eye scroll pattern by performing the eye tracking using a plurality of images of the user captured while the first content is displayed; and
   comparing the detected eye scroll pattern to a predefined eye scroll pattern for the displayed first content.

3. The method of claim 1, wherein the displaying the second content comprises changing a brightness or contrast of the second content.

4. The method of claim 1, wherein the image comprises a video for the user, and
   wherein the information regarding the wrinkle is obtained from the video.

5. The method of claim 1, wherein the displaying the second content comprises:
   obtaining a visual acuity value for the user based on the information regarding the wrinkle; and
   in response to the visual acuity value exceeding a threshold value, displaying the second content according to the visual acuity value.

6. The method of claim 5, further comprising:
   tracking the visual acuity value for the user over a period of time.

7. The method of claim 5, wherein the obtaining the visual acuity value comprises:
   obtaining sensor data; and
   obtaining the visual acuity value based on the sensor data and the information regarding the wrinkle.

8. The method of claim 1, further comprising:
   identifying information regarding a display setting based on the information regarding the wrinkle; and
   transmitting, to a server, the information regarding the display setting.

9. The method of claim 1, further comprising:
   displaying a third content for recommend to check eyesight.

10. An electronic device comprising:
    a camera;
    a display; and
    at least one processor operatively coupled with the camera and the display,
    wherein the at least one processor is configured to control to:
       obtain an image of a face of a user viewing a first content,
       obtain information regarding a wrinkle on a skin of the user based on an analysis on the obtained image using an algorithm, and
       display a second content, wherein the second content is a content in which the first content is enlarged according to the information regarding the wrinkle,
       wherein the at least one processor is configured to display the second content by:
          using an artificial intelligence (AI) algorithm based on the information regarding the wrinkle, and
          displaying the second content according to an output of the AI algorithm.

11. The electronic device of claim 10, wherein the at least one processor is configured to control to:
    determine that the user views the first content displayed on the electronic device by an eye tracking,
    detect an eye scroll pattern by performing the eye tracking using a plurality of images of the user captured while the first content is displayed, and
    compare the detected eye scroll pattern to a predefined eye scroll pattern for the displayed first content.

12. The electronic device of claim 10, wherein the at least one processor is configured to control to change a brightness or contrast of the second content.

13. The electronic device of claim 10, wherein the image comprises a video for the user, and
    wherein the information regarding the wrinkle is obtained from the video.

14. The electronic device of claim 10, wherein the at least one processor is configured to control to:
    obtain a visual acuity value for the user based on the information regarding the wrinkle; and
    in response to the visual acuity value exceeding a threshold value, display the second content according to the visual acuity value.

15. The electronic device of claim 14, wherein the at least one processor is further configured to control to track the visual acuity value for the user over a period of time.

16. The electronic device of claim 14, wherein the at least one processor is configured to:
    obtain sensor data, and
    obtain the visual acuity value based on the sensor data and the information regarding the wrinkle.

17. The electronic device of claim 10, further comprising a transceiver,
    wherein the at least one processor operatively coupled with the transceiver is configured to control to:

identify information regarding a display setting based on the information regarding the wrinkle; and transmit, to a server, the information regarding the display setting.

18. The electronic device of claim 10, wherein the at least one processor is further configured to display a third content for recommend to check eyesight.

* * * * *